(12) United States Patent
Chang

(10) Patent No.: US 11,398,297 B2
(45) Date of Patent: Jul. 26, 2022

(54) SYSTEMS AND METHODS FOR USING MACHINE LEARNING AND DNA SEQUENCING TO EXTRACT LATENT INFORMATION FOR DNA, RNA AND PROTEIN SEQUENCES

(71) Applicant: Chun-Chieh Chang, South San Francisco, CA (US)

(72) Inventor: Chun-Chieh Chang, South San Francisco, CA (US)

(*) Notice: Subject to any disclaimer, the term of this patent is extended or adjusted under 35 U.S.C. 154(b) by 553 days.

(21) Appl. No.: 16/595,873

(22) Filed: Oct. 8, 2019

(65) Prior Publication Data
US 2020/0118648 A1    Apr. 16, 2020

Related U.S. Application Data

(60) Provisional application No. 62/744,180, filed on Oct. 11, 2018.

(51) Int. Cl.
*G16B 40/20* (2019.01)
*G06N 3/08* (2006.01)
(Continued)

(52) U.S. Cl.
CPC ........... *G16B 40/20* (2019.02); *G06N 3/0454* (2013.01); *G06N 3/08* (2013.01); *G16B 30/00* (2019.02)

(58) Field of Classification Search
CPC ........ G16B 30/00; G16B 20/00; G16B 15/00; G16B 15/30; G16B 40/20; G16B 40/30; G06N 3/04; G06N 20/00; G06N 5/022; G06N 20/10; G06N 3/126; G06N 3/0454; G06N 3/08
See application file for complete search history.

(56) References Cited

U.S. PATENT DOCUMENTS

| | | | |
|---|---|---|---|
| 2003/0022200 A1* | 1/2003 | Vissing | G16B 25/30 435/6.1 |
| 2004/0161796 A1* | 8/2004 | Gustafsson | G16B 35/00 435/7.1 |

(Continued)

FOREIGN PATENT DOCUMENTS

| CN | 111048151 A | * | 4/2020 | |
|---|---|---|---|---|
| CN | 112837747 A | * | 5/2021 | |
| WO | WO-2019099716 A1 | * | 5/2019 | ........... G06K 9/0014 |

OTHER PUBLICATIONS

Deep Neural Network Based Predictions of Protein Interactions Using Primary Sequences (Year: 2018).*

(Continued)

*Primary Examiner* — Nizar N Sivji
(74) *Attorney, Agent, or Firm* — Burris Law, PLLC

(57) ABSTRACT

A method of characterizing biological sequences includes: preparing a library of sequences; subjecting the sequences in the library to at least one screening experiment to obtain an experiment outcome of each of the sequences; creating a first dataset comprising identities of the sequences and the experiment outcomes of the sequences; and training a first neural network using the first dataset to extract first sequence features from the sequences in the first dataset. A second neural network may be additionally trained using a second dataset based on an external database to generate a pre-trained model, which is used extract additional features from the first dataset.

11 Claims, 8 Drawing Sheets

(51) Int. Cl.
*G06N 3/04* (2006.01)
*G16B 30/00* (2019.01)

(56) References Cited

U.S. PATENT DOCUMENTS

| | | | | |
|---|---|---|---|---|
| 2005/0053999 | A1* | 3/2005 | Gough | C40B 30/04 435/6.16 |
| 2008/0097939 | A1* | 4/2008 | Guyon | G06K 9/6269 706/12 |
| 2009/0082975 | A1* | 3/2009 | Balac Sipes | G16B 40/00 702/20 |
| 2010/0256988 | A1* | 10/2010 | Barnhill | G16H 10/40 706/54 |
| 2011/0184896 | A1* | 7/2011 | Guyon | G06K 9/6231 706/12 |
| 2011/0224913 | A1* | 9/2011 | Cui | G16B 20/00 702/19 |
| 2013/0332133 | A1* | 12/2013 | Horn | G16B 50/00 703/11 |
| 2016/0333405 | A1* | 11/2016 | Quake | G16B 20/20 |
| 2017/0076036 | A1* | 3/2017 | Theofilatos | G06N 20/00 |
| 2017/0211206 | A1* | 7/2017 | Cope | G16C 20/60 |
| 2018/0321245 | A1* | 11/2018 | Guyon | C12Q 1/6886 |
| 2019/0371429 | A1* | 12/2019 | Azab | G16B 30/00 |

OTHER PUBLICATIONS

On the prediction of DNA-binding proteins only from primary sequences: A deep learning approach—2017 (Year: 2017).*
RNA-protein binding motifs mining with a new hybrid deep learning based cross-domain knowledge integration approach—2017 (Year: 2017).*
A Novel Approach for Protein Structure Prediction—2010 (Year: 2010).*
High-throughput discovery of functional disordered regions: investigation of transactivation domains 2018 (Year: 2018).*
How Will Bioinformatics Impact Signal Processing Research?—2013 (Year: 2013).*
Interpretable Machine Learning Methods for Regulatory and Disease Genomics—Jun. 2018 (Year: 2018).*
Machine Learning in Bioinformatics: A Novel Approach for DNA Sequencing—2015 (Year: 2015).*
Applications of ANN and RULES-3 to DNA Sequence Analysis—2009 (Year: 2009).*
Bioinformatics With Soft Computing—2006 (Year: 2006).*
De novo profile generation based on sequence context specificity with the long short-term memory network—2018 (Year: 2018).*
Gene prediction using Deep Learning—Jul. 2018 (Year: 2018).*

* cited by examiner

SYSTEMS AND METHODS FOR USING MACHINE LEARNING AND DNA SEQUENCING TO EXTRACT LATENT INFORMATION FOR DNA, RNA AND PROTEIN SEQUENCES

CROSS-REFERENCE TO RELATED APPLICATION

This application claims the benefit of U.S. Provisional Application No. 62/744,180, filed Oct. 11, 2018, and titled "Systems and Methods for Using Machine Learning and DNA Sequencing to Extract Latent Information for DNA and Protein Sequences," the content of which is incorporated herein by reference in its entirety.

FIELD

The present disclosure relates generally to the field of DNA, RNA, and amino acids sequence screening, and more specifically to an improved and useful system and method for extracting structural and higher order latent information for each sequence from a pool of sequences.

BACKGROUND

The statements in this section merely provide background information related to the present disclosure and may not constitute prior art.

Typically, locating one or more DNA, RNA or protein sequences (either natural or unnatural nucleotides or amino acids) with a desired outcome often relies on designing a pool of sequences and conducting experiments using those sequences. A pool of sequences is called a library. The sequences may be natural or unnatural nucleotides or amino acids. The sequences in the library are usually slightly different from each other. The differences can be as small as a single position difference between two sequences or can have two sequences that are entirely different in each position and can also have different lengths.

During a screening experiment, researchers typically combine the library (or libraries) with target samples, and then locate and quantify which sequences in the library interact with the target samples. For example, in order to locate sequences that bind to a receptor protein on a cancer cell or to locate sequences that can effectively shutdown a cellular function, researchers conventionally create a pool of sequences and subject them to desired targets, and then collect those sequences that can interact with the targets. The sequences collected through one round of experiment, however, may still contain non-specific or false-positive results. Therefore, researchers often need to conduct additional two or more rounds of the same experiment using collected sequence in order to amplify true-positive sequences.

Locating a small subset of sequences with the desired characteristics is time-consuming and requires multiple rounds of screening and library design. This is often due to high background noise or low detection sensitivity during each screening experiment. Therefore, by doing multiple rounds of screening experiments, the signal from "desired" sequences may be amplified.

To improve the efficiency of locating the sequences with the described characteristics, one method is to group similar sequences together. Instead of analyzing individual sequences across $10^5$-$10^{11}$ sequences, we can narrow our search by focusing on smaller subset of groups. A conventional grouping (or clustering) method relies on sequence alignment technique, which is based on comparing individual nucleotide or amino acid at each position to another sequence, and then calculate a similarity score. The alignment can be done by aligning and comparing sequences in the library to each other in the library, or it can be done by comparing sequences in the library to sequences in the public database.

However, the sequence alignment method only considers sequence similarity at character level, without considering higher order interactions within each sequence. Moreover, some newly designed libraries are very novel and may be completely different from sequences existing in the public database. In that case, aligning the sequences in the library to the publicly available sequences is impossible. Furthermore, some biophysical properties (such as cell toxicity) cannot be discovered and assessed by sequence alignment, and thus additional experiments are required to assess several biophysical properties. As a result, locating the "desired" target sequences has been proven inefficient.

The above-mentioned issues are addressed in the present disclosure.

SUMMARY

In one form, the present disclosure provides a method of characterizing biological sequences includes: preparing a library of sequences; subjecting the sequences in the library to at least one screening experiment to obtain an experiment outcome of each of the sequences; creating a first dataset comprising identities of the sequences and the experiment outcomes of the sequences; and training a first neural network using the first dataset to extract first sequence features from the sequences in the first dataset.

In other features, the method further include: pre-training a second neural network using a second dataset different from the first dataset to obtain a pre-trained model; extracting second sequence features from the first dataset using the pre-trained model; and using these sequence features to group similar sequences and re-designing a more specific library that enhances the desired sequence features and outcome. The second dataset is obtained from an external and public dataset. The second sequence features are different from the first sequence features.

It should be noted that the features which are set out individually in the following description can be combined with each other in any technically advantageous manner and set out other variations of the present disclosure. The description additionally characterizes and specifies the present disclosure, in particular in connection with the figures.

Further areas of applicability will become apparent from the description provided herein. It should be understood that the description and specific examples are intended for purposes of illustration only and are not intended to limit the scope of the present disclosure.

DRAWINGS

In order that the disclosure may be well understood, there will now be described various forms thereof, given by way of example, reference being made to the accompanying drawings, in which.

Figure 1:
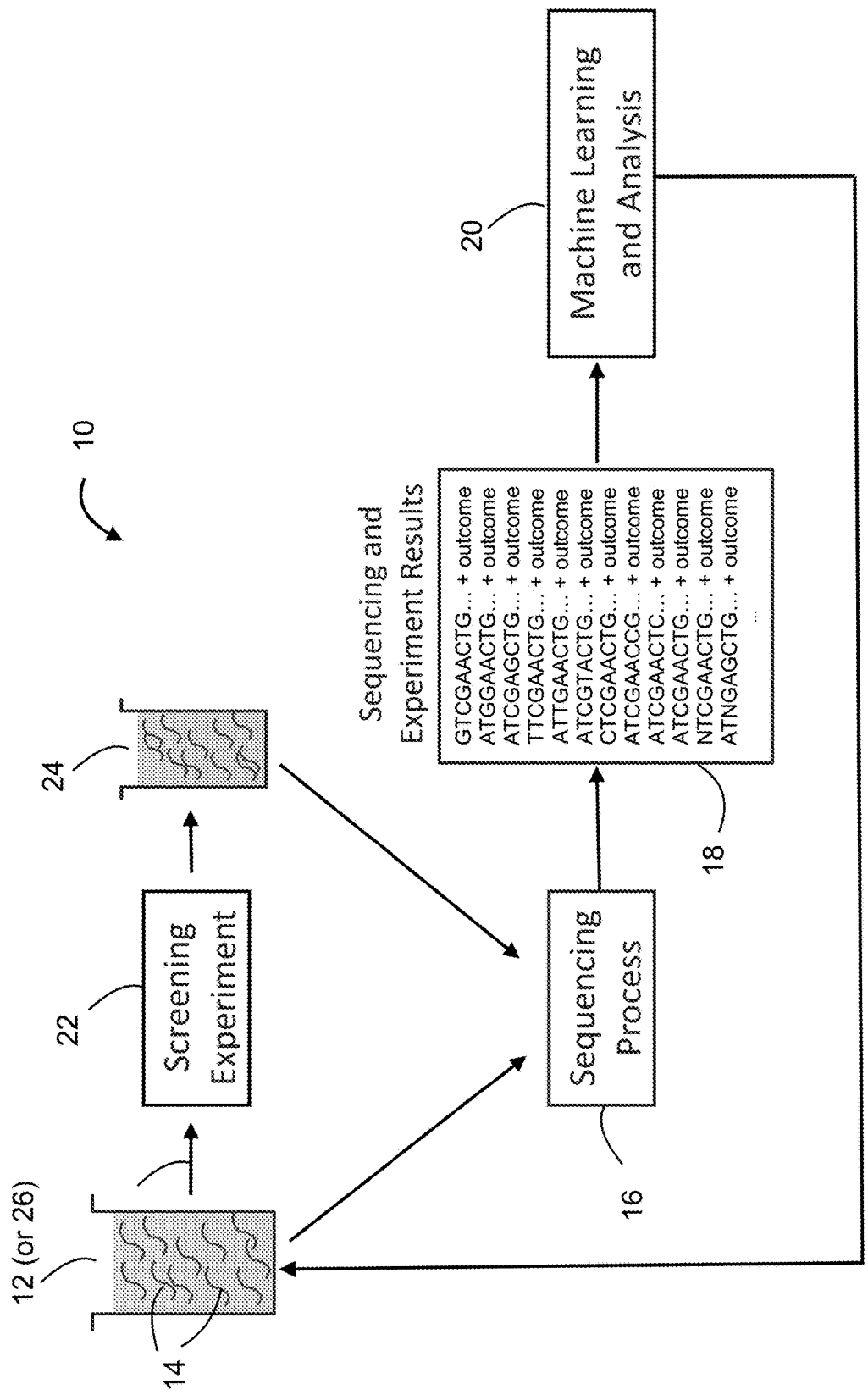
FIG. 1 is a schematic diagram depicting steps of preparing a first dataset for a machine learning and analysis process in accordance with the teachings of the present disclosure.

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features.

Referring to FIG. 1, a method of characterizing molecules with biological sequences (hereinafter "sequences") in accordance with the teachings of the present disclosure starts with creating a first dataset 18 for a machine learning and analysis process 20. The first dataset 18 is created by: preparing at least one library 12 of sequences 14; determining identities of the sequences 14 in the at least one library 12 by a sequencing process 16; subjecting the sequences 14 in the at least one library 12 to at least one screening experiment 22; and obtaining an experiment outcome for each of the sequences 14 in the at least one library 12.

A library 12 is a pool of molecules each having a sequence 14. The sequences 14 may include, but be not limited to, DNA, RNA, or proteins. DNA and RNA sequences can be made of natural or unnatural nucleotides. Protein sequences can be made of natural and unnatural amino acids. The unnatural molecules are modifications of natural molecules and may be made by chemical synthesis technology. A library usually contains $10^5$ to $10^{11}$ unique molecules. The library 12 may contain a single copy or multiple copies of each sequence. It is understood that any number of sequences may be contained in the library 12 without departing from the scope of the present disclosure. The difference between each molecule/sequence can range from having only a single position difference (e.g., ATCGAATT vs. ATCGATTT) to having two very different sequences (e.g., ATCGAATT vs. TTAAGCTA). These sequences in the library 12 may, but not necessarily, be encoded in plasmids, virus's genome, bacteria's genome, or any other forms that can carry nucleotide sequences information. The library 12 can also contain direct synthetic nucleotide sequences or amino acid sequences.

The plurality of sequences 14 in the library 12 may be subjected to a sequencing process 16. The sequencing process 16 is optional depending on whether the identities of the sequences 14 in the library 12 are determined or confirmed.

The sequencing process 16 is needed when the library 12 contains freshly generated sequences 14 whose identity have yet to be determined and quantified. The sequencing process 16 may also be needed when a distribution of the molecules with sequences in the library 12 has been changed as a result of at least one screening experiment 22 being conducted on the sequences 14 in the library 12 (which will be described in more detail below). Therefore, it is necessary to re-quantify and re-identify what are left in the library after the screening experiment 22. If the sequence identity of each molecule is already known, the sequencing process 16 may be eliminated.

DNA sequencing is the process of determining the precise order of the four bases—adenine, guanine, cytosine, and thymine (A, T, G, C) in a strand of DNA. Similarly, RNA and protein sequencing is the process of determining the precise order of the bases from which RNA or protein is composed. A sequencer for performing the sequencing process 16 may be, for example, a next-generation sequencing machine such as Illumina, Ion semiconductor sequencing (also called Ion-Torrent sequencing), or nano-pore sequencers. Any sequencers that can determine the sequences of the molecules may be used without departing from the scope of the present disclosure.

On the other hand, after the library 12 is prepared, the molecules in the library 12 may be subjected to at least one screening experiment 22. The screening experiment 22 may be used to identify any sequences 14 in the library 12 that can interact with a target of interest. The experiment outcome for each sequence after the screening experiment 22 refers to the information about interaction or non-interaction with the target of interest. The target or targets of interest can be, but not limited to, a cell or cells, a protein on the cell, a location or region of a genome in the cell etc. The interaction usually refers to the binding of molecules in the library 12 to the target. After the screening experiment 22, a smaller pool 24 of sequences may be created, which includes only sequences that can interact with a target of interest.

For example, in order to find one or more antibody drugs that have high affinity binding to an antigen on a cancer cell, an antibody phage display screening experiment is usually conducted. In this screening experiment 22, a library 12 may contain $10^{11}$ different molecules of viruses, each virus expresses one unique type of protein on the virus surface. In other words, the library 12 contains $10^{11}$ different protein sequences 14. The target in this experiment may be the antigen expresses on the cancer cell.

In this case, the screening experiment 22 involves incubating the molecules in the library 12 with the target antigen in order to identify those proteins that can bind to the target antigen. As a result, a smaller pool 24 of protein sequences that can interact with the target antigen is created. The experiment outcome in this example is the measure of abundance of each sequence in the pool. The more abundant of a sequence may infer that sequence is likely to interact/bind to the target antigen. However, it can still be time consuming to identify proteins that can truly interact with the target antigen from the smaller pool 24 of potential binders.

As another example, in clustered regularly interspaced short palindromic repeats (CRISPR) screening, a library 12 of guide-RNA may be prepared. The guide-RNA may modify or delete their target genes in the screening experiment 22. Some guide RNA can efficiently modify their corresponding genes, while some may have little effect. The target in this example is the gene that each guide RNA interacts with. The outcome is the modifying efficiency which is measured by the sequencing process 16. Often times the gene editing/modifying efficiency is very low, and researchers have to repeat the experiments many times in order to collect successful edited gene. A method for identifying guide RNA and target gene sequence features that lead to high modifying efficiency is needed.

After the sequencing process 16 and the screening experiment 22, the information relating to the identities of the individual sequences 14 and the outcomes of the individual sequences are collected to create a first dataset 18. The first dataset 18 comprises both sequence identities determined by the sequencing process 16 and the experiment outcomes determined by the screening experiment 22. Alternately, the first dataset 18 can also be data aggregated from different screening experiments or databases where identities of individual sequences are already known. The first dataset 18, after being converted into digital data, is sent to a machine learning and analysis module 40 (shown in FIG. 2) for training purposes. As will be described in more detail below, the insight obtained from the machine learning and analysis process 20 will also help understand the experiment and can aid re-designing a more focused library 26 for better outcome.

Figure 2:
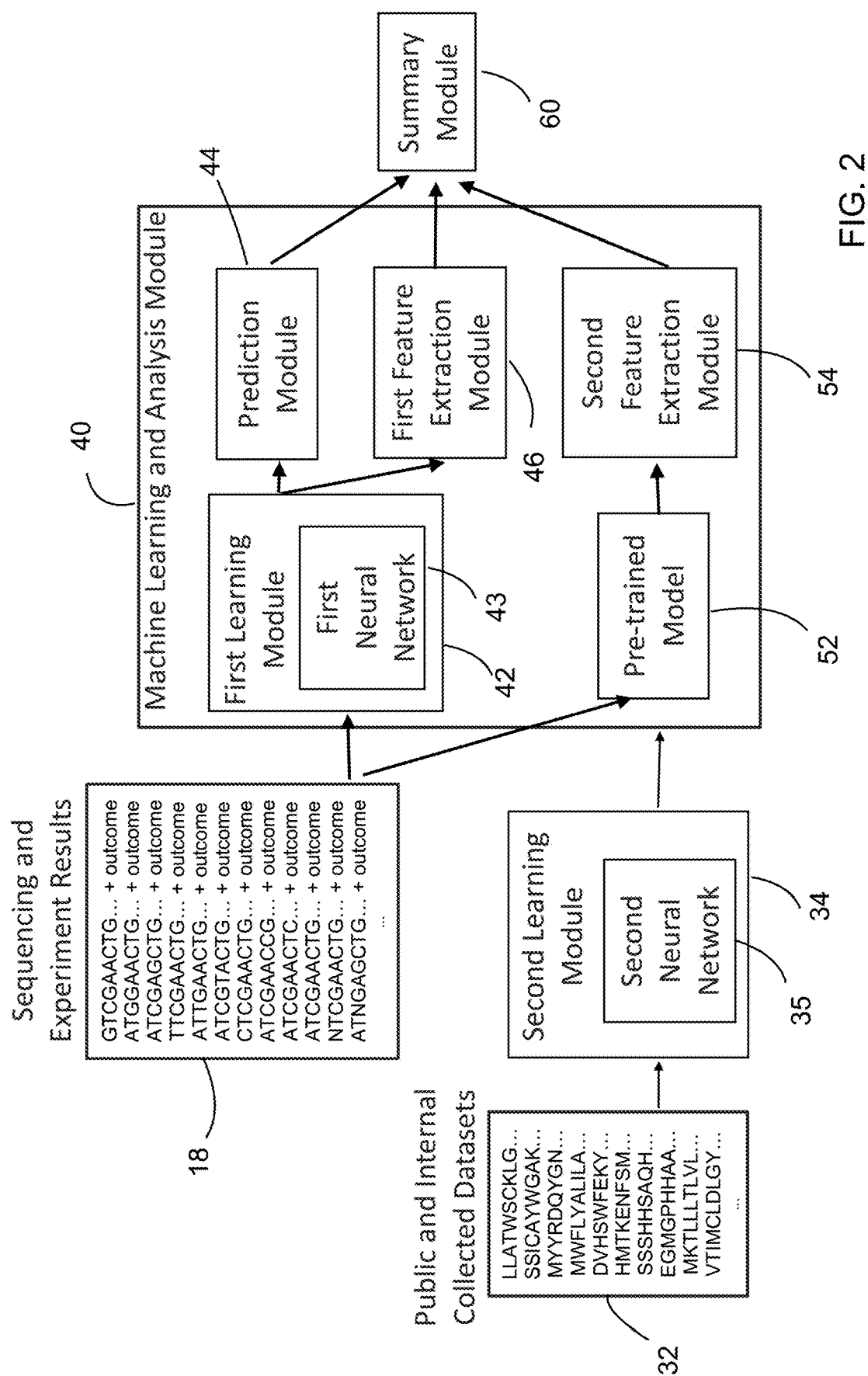
FIG. 2 is a schematic diagram of a machine learning and analysis module for characterizing sequences, extracting features, and predicting outcomes of the sequences in accordance with the teachings of the present disclosure.

Referring to FIG. 2, the machine learning and analysis module 40 can be trained using the first dataset 18 to learn a relationship between the experiment outcomes and the sequences 14. It is understood that the first dataset 18 need to be converted into digital data before it can be processed by algorithms of the machine learning and analysis module 40. The relationship between the experiment outcome and the sequences is also called the "sequence features" or "characteristics of the sequences." The characteristics include, but are not limited to, 2D and 3D structural information of each sequence, motif interaction score, dimer, trimer, or k-mer information score, physical and chemical scores. Sequences 14 can then be clustered or grouped based on these rich information of each sequence 14. Additional sequence features, such as cell toxicity motif, cell membrane binding motif, DNA binding motif, may be further learned by using another dataset and another machine learning model, which will be described in more detail below.

As further shown, the machine learning and analysis module 40 includes a first learning module 42, a prediction module 44, a first feature extraction module 46, a pre-trained model 52, and a second feature extraction module 54. The first learning module 42 includes a first neural network 41, which is trained using the first dataset 18 to output a trained model. The pre-trained model 52 is an output from a second training module 34 including a second neural network 35. The second neutral network 35 is pre-trained using a second dataset 32. The second dataset 32 comprises sequences from publicly available datasets. As an example, the second dataset can include sequences that are related to cell toxicity, cell membrane binding, metal binding, DNA binding, RNA binding, and non-specific binding to any molecules.

The pre-trained model 52 is included in the machine learning and analysis module 40 to learn additional sequence features from the first dataset 18, which may not be revealed by the screening experiment 22.

The first neural network 43 includes a plurality of architectures including a plurality of layers. The first layer takes the sequences 14 as input data. Given each input data, the last layer of the first neural network 43 can have two outputs at the same time: one for predicted experimental outcome, and the other for reassembled input sequence. A plurality of encoder layers are provided between the first and last layers to transform input sequence into smaller and smaller feature spaces. The last encoder layer is connected to the last layer to reassemble (predict) the input sequences and to predict the experimental outcome for each input sequence. Each layer can be considered a new feature space, and each layer captures different feature of the sequence. Generally, earlier layers capture basic sequence properties such as molecular weight, hydrophobicity etc., while latter layers capture higher dimensional feature such as 3D structure and motif-motif interactions. The model architecture will be described in more detail below in connection with FIG. 3.

After the first neural network 43 is properly trained (i.e., its predicted outputs are close to the experimental outputs and input sequence, with a difference below a predetermined threshold and with the difference not capable of being minimized), the first learning module 42 may output a learned model to the prediction module 44, which can make prediction on the outcomes of new sequences using the learned model without the need to conduct a screening experiment. For example, researchers may design a new library of sequences and use the learned model of the prediction module 44 to predict whether the new library of sequences is of interest (such as sequences having desired characteristics) for further research.

In addition to the trained model, the first neural network 43 of the first learning module 42 also outputs sequence features captured in each layer of the first neural network 43 to the first feature extraction module 46. The first feature extraction module 46 may use these layers to learn what sequence features result in good experimental outcomes. Alternatively, the first feature extraction module 46 may use the feature information to group or cluster sequences with similar features and conduct further research on smaller groups of sequences. This is different from traditional sequence alignment, where the definition of "similar sequences" is often based on alphabetical similarity. Here, the similarity is based on learned sequence features, which can contain 2D and 3D structural information, motif information, physical and chemical properties. Hence, our grouping method should provide more biological relevant similarity. Not only are these sequence features useful for grouping and sequences clustering, this information is also useful for researchers to learn why certain sequences result in poor outcome and certain sequences result in good outcome. The researchers can then use these sequence features to create a more targeted sequence library 26 as depicted in FIG. 1 and repeat the screening procedure to obtained sequences with desired outcomes.

A potential limitation of the first feature extraction module 46 is that those features extracted may be limited to the experimental design. For example, in the antibody and cell surface antigen binding scenario, the extracted features are mostly related to whether a given sequence has special motif that can interact with the target antigen. It does not consider whether the antibody sequence may cause cell toxicity and whether the antibody sequence may penetrate and disrupts the cell membrane.

In order to provide more sequence features, the pre-trained model 52 may be included in the machine learning and analysis module 40. As previously described, the pre-trained model 52 is an output of the second neural network 34 of the second training module 34, which is pre-trained using a second dataset 32 obtained from external and public datasets.

The training process of the second neural network 34 is similar to that of the first neural network 43 of the first training module 42, except that the second dataset 32 used for this training does not necessarily have any outcome information. In other words, the second dataset 32 includes sequences without any associated outcome regarding the interaction or non-interaction with a target of interest. This is a type of unsupervised machine learning model, which can be learned by using multiple layers of encoder and decoder. In such case, the model training is the process of learning to extract features of input sequences and use extracted features to re-assemble original input sequences. In contrast, the training process of the first neural network 43 of the first learning module 42 is a combination of supervised and unsupervised machine learning process. After the training of the second neural network 35, the pre-trained model 52 can be included in the machine learning and analysis module 40 for extracting additional sequence features from the first dataset 18.

A summary module 60 may be provided to be in communication with the prediction module 44, the first feature extraction module 46, and the second feature extraction module 54 to generate an output for the user. The output of the summary module 60 may be, but be not limited to, an electronic report describing the sequence feature for each sequence, predicted outcome for newly designed sequences. It can also include graphs that highlight specific amino acids or DNA nucleotides that constitute specific sequence features.

Figure 3:
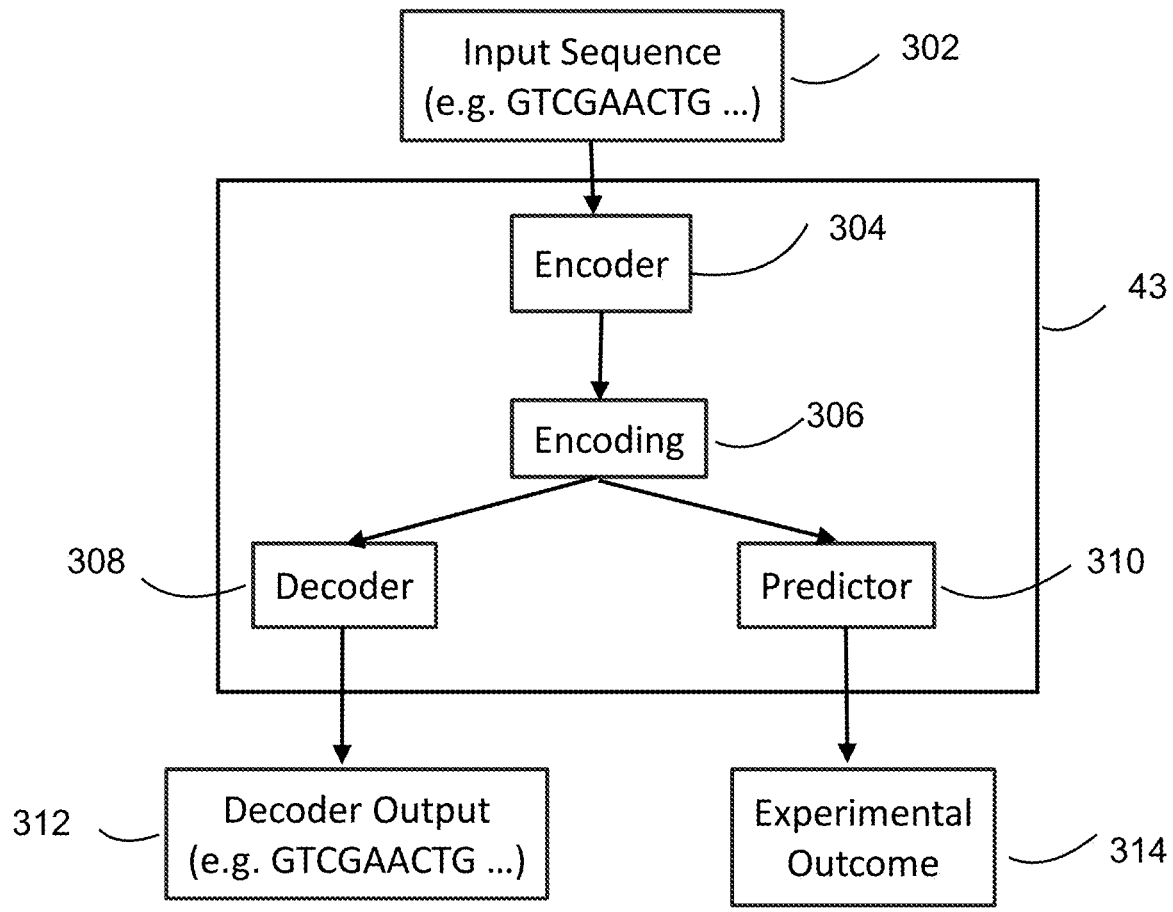
FIG. 3 is a schematic diagram of an exemplary first neural network of a first training module of the machine learning and analysis module of FIG. 2.

Referring to FIG. 3, an exemplary first neural network 43 of the first learning module 42 is illustrated. The first neural network 43 is configured to provide two functions: 1. encoding each input sequence into a vector of numbers; 2. finding relationship between input sequences and their corresponding experimental outcomes.

The first neural network 43 of the first learning module 42 is trained by taking in a given input sequence 302, passing it through an encoder 304, converting the sequence into an encoding 306 which is a vector of numbers, and then passing these numbers to a decoder 308 in order to optimize the similarity of input sequence 302 and its decoded output sequence 312. Concurrently, the first neural network 43 of the first learning module 42 can optimize its ability to predict encoding 306 to its corresponding experimental outcome 314 by training a predictor 310. Steps 302, 304, 306, 308, and 312 are common workflows called autoencoders. The encoding and decoding procedure can include many variations such as variational autoencoder (VAE) and adversarial autoencoder (AAE). The architectures of encoder 304, decoder 308, and predictor 310 can be any number of multi-layer perceptrons, convolutional neural networks, and recurrent neural networks.

After the first neural network 43 is trained, the first training module 42 outputs a trained model to the prediction module 44 such that the prediction module 44 can make prediction on the outcome of a new sequence based on the trained model. In addition, the trained model can also be output to the first feature extraction module 46 such that the first feature extraction module 46 can extract features from each sequence. The function of the first feature extraction module 46 is to group and cluster similar sequences as well as to find sequence motifs that are related to experimental outcomes. Therefore, the first feature extraction module 46 performs a grouping process and a process of extracting sequence features.

Figure 4:
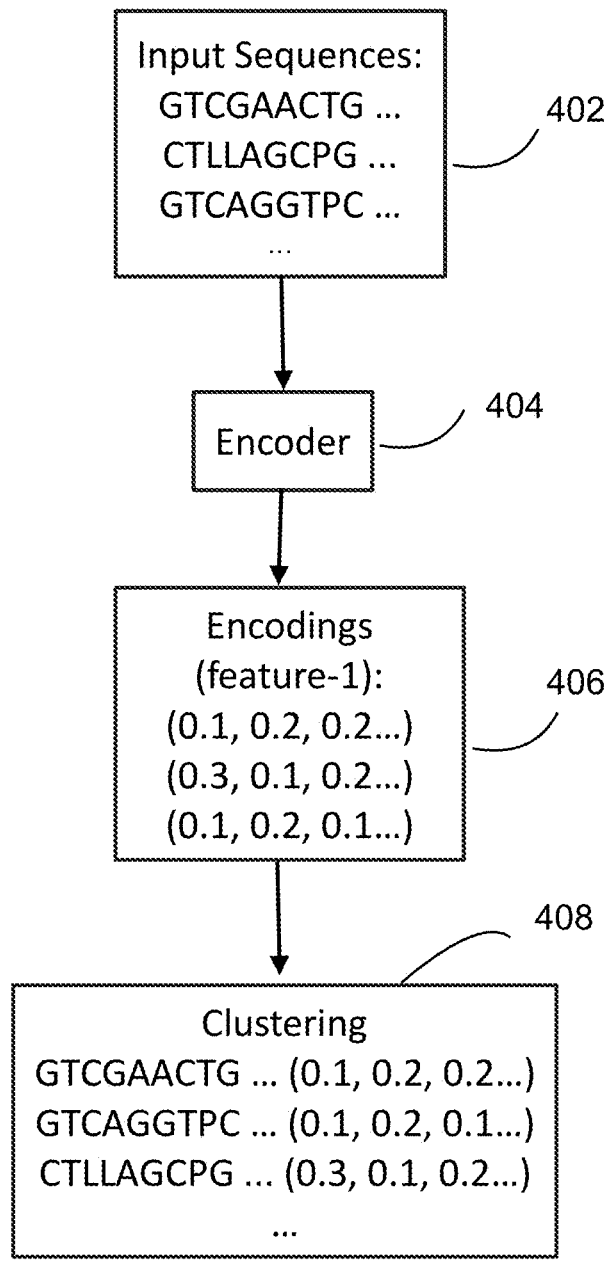
FIG. 4 is a flow chart of an exemplary grouping process performed by a first feature extraction module of the machine learning and analysis module of FIG. 2.

Referring to FIG. 4, an exemplary grouping process performed by the first feature extraction module 46 is illustrated. In the grouping process, the sequences 402 from the experiment are encoded by the trained encoder 404 to generate their encodings 406. At least one clustering step 408 is performed to group similar encodings in the same group. The sequence feature, such as motif features, for each sequence may be obtained by calculating the gradient for each position of the input sequence. The gradient for each position means how significant a small perturbation at that position can lead to a change in its encoding values.

Figure 5:
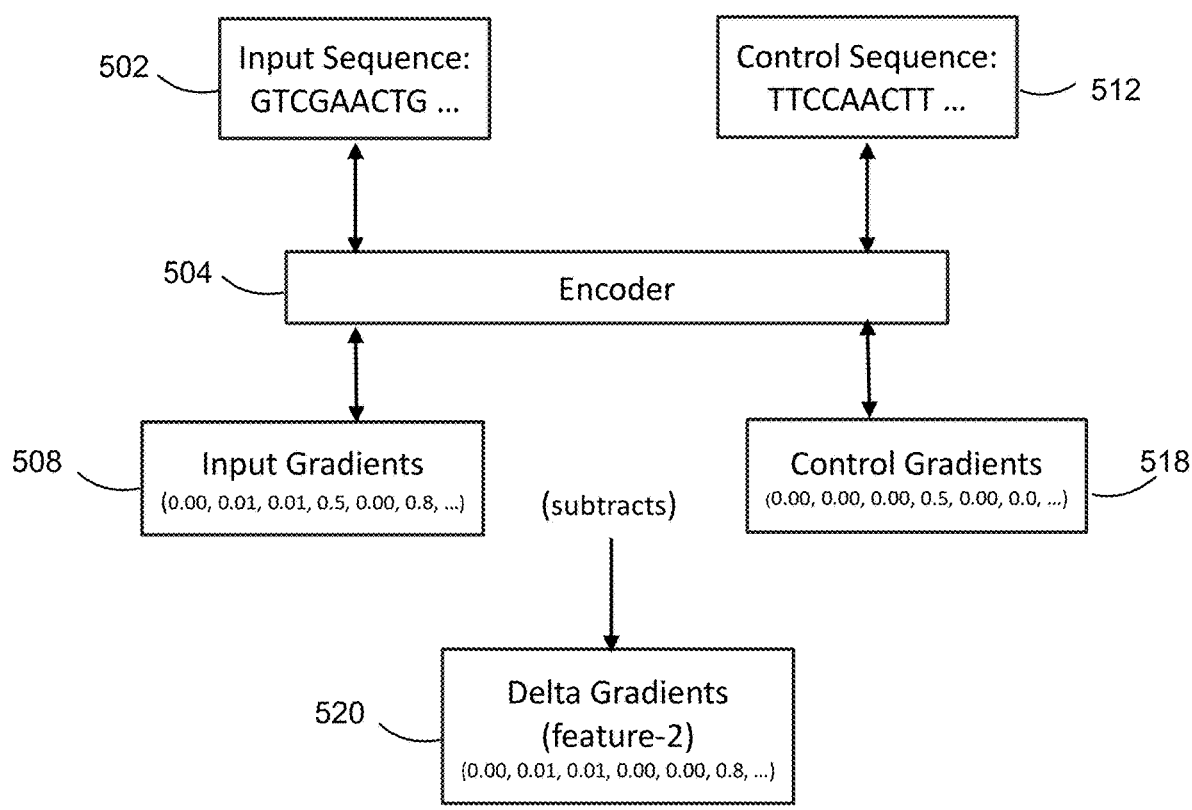
FIG. 5 is a flow chart of an exemplary process of extracting sequence features performed by a first feature extraction module of the machine learning and analysis module of FIG. 2.

Referring to FIG. 5, an exemplary process of extracting sequence features performed by the first feature extraction module 46 of the machine learning and analysis module 40 is illustrated. The gradients with respect to a sample sequence 508 and a control sequence 518 may be calculated by a trained encoder 504. To obtain input sequence feature, we need to subtract out the gradient of control sequences 518 from the gradient of the sample sequence 508 produces the delta gradient 520. This delta gradient is then back-propagated (backward arrows) to the input sequence to obtain the input sequence feature.

Figure 6:
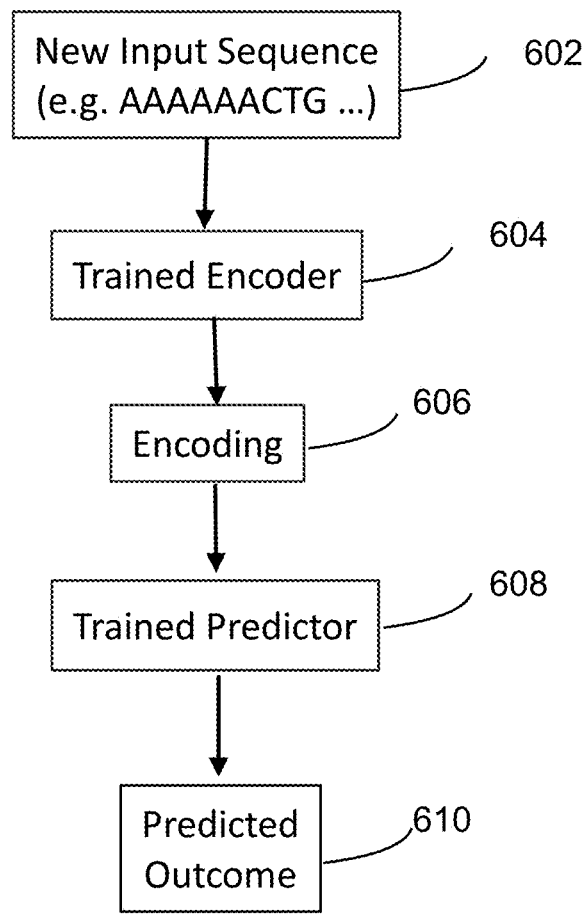
FIG. 6 is a flow chart of a prediction process performed by the prediction module of the machine learning and analysis module of FIG. 2.

Referring to FIG. 6, an exemplary prediction process performed by the prediction module 44 is illustrated. The prediction module 44 is configured to take any new sequences 602, pass them through a trained encoder 604 to obtained their encodings 606, and then pass the encodings 606 through a trained predictor 608 to get predicted outcomes. All the feature extraction and prediction results are further summarized in the summary module 60.

Figure 7:
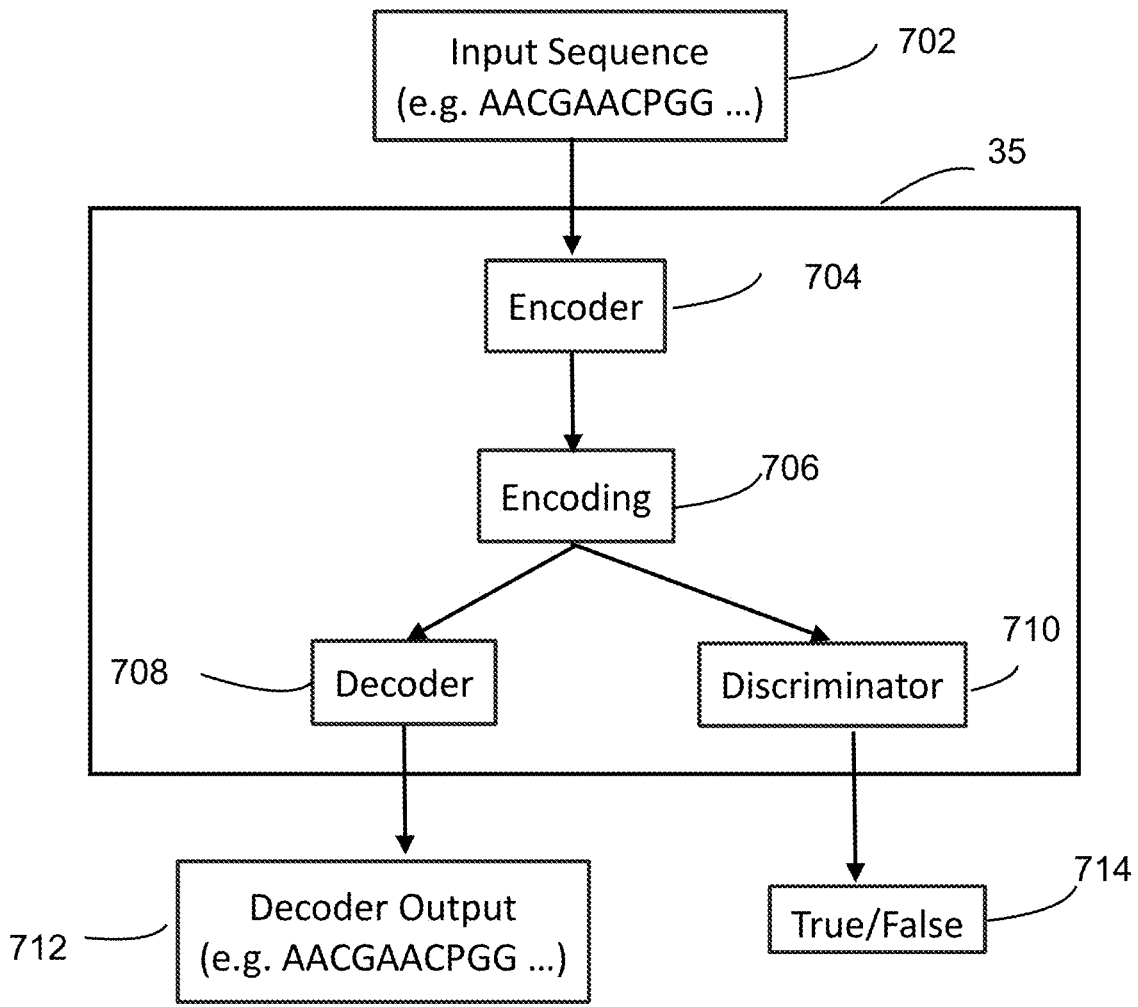
FIG. 7 is a schematic diagram of an exemplary second neural network of a second training module.

Referring to FIG. 7, an exemplary second neural network 35 of the second training module 34 is illustrated. As previously described, in addition to features obtained from the screening experiment 22, additional features can be extracted from the collected datasets 32 using the second neural network 35. If the collected data has a pair of both sequence and outcome, the model is trained just like training the first neural network model 43 of the first training module 42 for our experimental data. However, if the collected data contains only sequences without any corresponding outcomes, a discriminator 710, instead of a classifier, can be used to optimize the encoder 704 for producing encoding 706 that can better represent the input sequence 702 from collected data. Concurrently, a decoder 708 can be trained to optimize the encoder 706 for producing encoding 706 that captures the identity of the input sequence 702. In the case of only sequence alone without any corresponding outcome, the second neural network 35 needs to include at least one of the decoder 708 and discriminator 710 in order to optimize the encoder 706. Similar to the first neural network 43 of the first training module 42, the second neural network 35 of the second training module 34 can have any number of layers of perceptrons, convolutional neural networks, and recurrent neural networks.

After the neural network model, specifically the encoder 704 of the neural network module, is trained with collected datasets 32, the second feature extraction module 54 can be used to extract additional motif features for each sequence. The process of extracting sequence features by the second feature extraction module 54 is similar to that described in FIG. 5 in connection with the first feature extraction module 46 and thus the description thereof is omitted herein for clarity.

Figure 8:
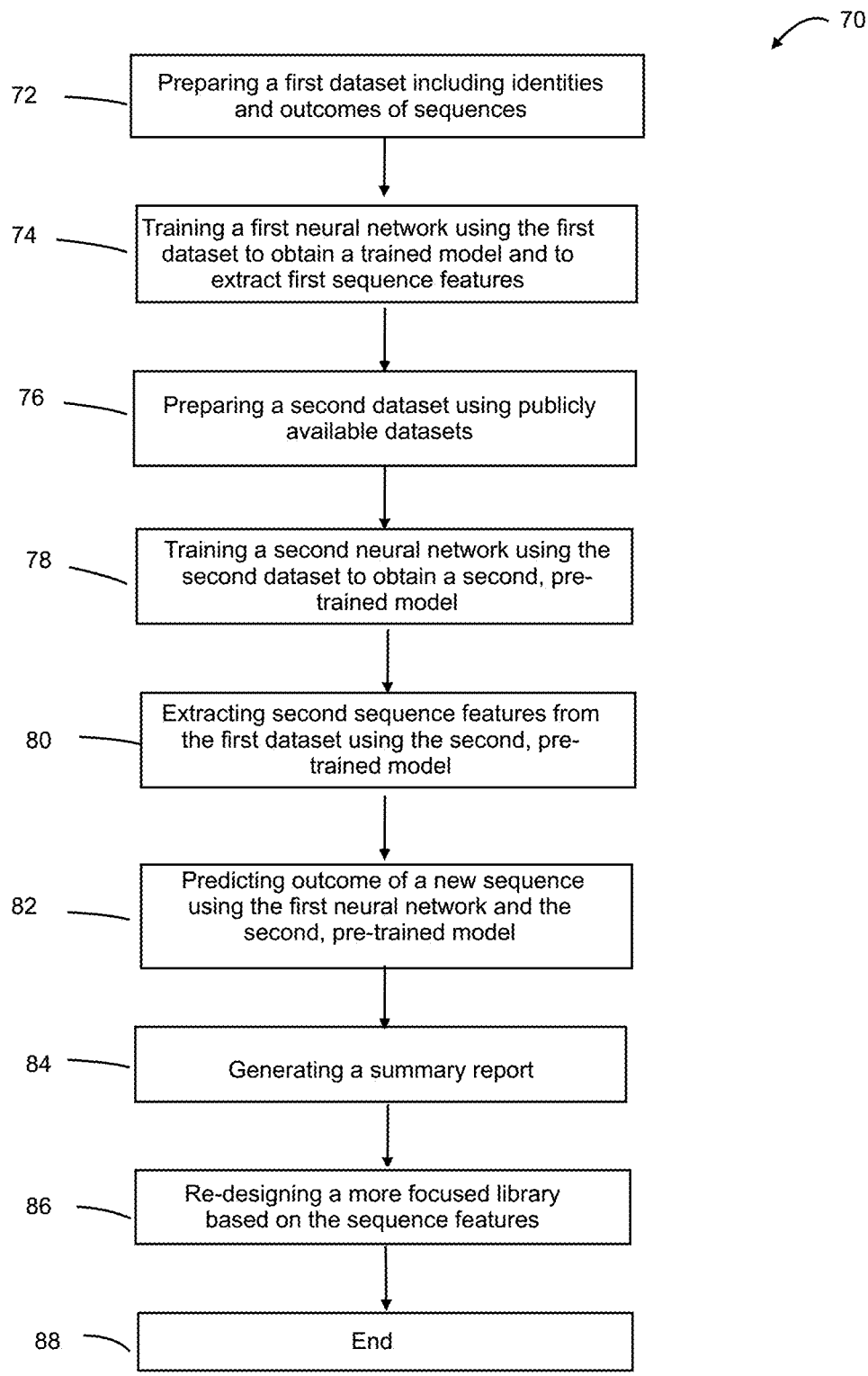
FIG. 8 is a flowchart of a method of characterizing biological sequences in accordance with the teachings of the present disclosure.

Referring to FIG. 8, a method 70 of characterizing molecules having biological sequences ("sequences") in accordance with the teachings of the present disclosure starts with preparing a first dataset 18 including sequence identities and outcomes in step 72. As previously described in connection with FIG. 1, the first dataset 18 is prepared by using a sequencing process to determine identities of the sequences and by subjecting the sequences to at least one screening experiments 22 to obtain outcomes of the sequences.

Next, a first neural network 43 is trained using the first dataset 18 to obtain a trained model and to extract sequence features in step 74. A second dataset 32 of sequences is prepared using publicly available datasets in step 76. A second neural network 35 is trained using the second dataset 32 to output a pre-trained model 52 in step 78. The second dataset is prepared using data from external and public datasets and internally connected. Additional (second) sequence features are extracted from the first dataset 18 using the second, pre-trained model 52 in step 80. The first neural network 43 and the second, pre-trained model 52 may also be used to predict outcome of new sequences in step 82. A summary report including first and second sequence features and predicted outcome of a new sequence may be generated in step 84. These sequence feature information can be used to design a more focused library with specific sequence features in step 86. The more focused library can be subjected to a new round of experiment to obtain better and desired outcomes. The method ends in step 88.

In summary, the method of the present disclosure includes two machine learning processes. A first learning process (supervised) use a first dataset 18 and a first neural network 43 to obtain a first trained model. A second learning process (unsupervised) uses a second dataset 32 and a second neural network 35 to obtain a second, or pre-trained model 52. The first dataset 18 includes identities of sequences and a quantitative experiment outcome (e.g. gene modification efficiency, abundance of protein binding) as shown in FIG. 1. The second dataset 32 includes identities of sequences obtained from external and public datasets and does not necessarily include experiment outcomes of the sequences. The second neural network 35 is pre-trained using the second dataset 32 and the pre-trained second neural network 35 may be used to extract additional sequence features that cannot be revealed by the screening experiment 22 when preparing the first dataset 18. A new library can be re-designed based on the sequence features identified by both the first and second neural network.

The machine learning process provides good insights about why certain sequences interact with the target and why other sequences do not interact with the target. This insight can help researchers re-design a more focused library including those specific sequence features identified by the first and second neural networks. These sequence features either from first dataset (based on experiment) or from the second dataset (based on external data)) can be used to group/cluster sequences with similar features into smaller subgroups. An experiment can be conducted again on the more focused library to obtain improved interaction between the sequences and the outcomes.

The more focused library based on the results of the machine learning process is advantageous particularly when the sequences are protein. Instead of grouping sequences based on how similar those sequences are, these sequences can be grouped based on how similar they are in terms of 2D, 3D structures, physical and chemical properties. The sequences may be grouped based these features and at those specific region of the sequences.

Therefore, a library with specific mutations can be designed. If the sequences are proteins, the mutation would be different amino acids. If the sequences are DNAs or RNAs, the mutation is nucleotides. This gives us a more focused library and should give us a better experimental result (e.g., binding to the target stronger and/or have less cell toxicity, or has less cell membrane binding etc.).

The system and method of the present disclosure provides high throughput sequence feature characterization and outcome prediction by machine learning and analysis based on target experiment, outcome collections and visualization. The system and method in accordance with the teachings of the present disclosure can characterize DNA, RNA and protein (either natural and unnatural amino acids) sequences without any prior knowledge of the characteristics of the sequences. Moreover, the system and method according to the present disclosure can extract latent sequence representation which may include sequence motif, 2D and 3D structural information from a sequence without any prior knowledge. Therefore, the system and method of the present disclosure can increase the efficiency in the screening process, thereby reducing costs.

The systems and methods of the preferred embodiment and variations thereof can be embodied and/or implemented at least in part as a machine configured to receive a computer-readable medium storing computer-readable instructions. The instructions are preferably executed by computer-executable components preferably integrated with the entire machine learning and analysis module as shown in FIG. 2. The computer-readable medium can be stored on any suitable computer-readable media such as RAMs, ROMs, flash memory, EEPROMs, optical devices (e.g., CD or DVD), hard drives, floppy drives, clouds (such as Google cloud or Amazon cloud), remote servers, or any suitable devices. The computer-executable component is preferably a general or application-specific processor, but any suitable dedicated hardware or hardware/firmware combination can alternatively or additionally execute the instructions.

The description of the disclosure is merely exemplary in nature and, thus, variations that do not depart from the substance of the disclosure are intended to be within the scope of the disclosure. Such variations are not to be regarded as a departure from the spirit and scope of the disclosure.

What is claimed is:

1. A method of characterizing molecules having sequences, the method comprising:
 preparing a first group of sequences;
 creating a first dataset comprising identities and experiment outcome of the sequences in the first group;
 creating a second dataset comprising identities of sequences from a second group of sequences obtained from publicly available datasets;
 training a first neural network using the first dataset to extract first sequence features from in the first dataset;
 training a second neural network using the second dataset to obtain a pre-trained model;
 extracting second sequence features using the pre-trained model and the first dataset;
 predicting an outcome of a new sequence based on a trained model obtained from the training of the first neural network;
 outputting a visualization report including the first and second sequence features and the predicted outcome of the new sequence;
 redesigning a more focused library based on the first and second sequence features; and
 conducting an experiment on the more focused library.

2. The method according to claim 1, wherein the second sequence features are different from the first sequence features.

3. The method according to claim 1, wherein the second dataset includes sequences that are related to at least one of cell toxicity, cell membrane binding, metal binding, DNA binding, RNA binding, and non-specific binding to any molecules.

4. The method according to claim 1, wherein the second sequence features are selected from a group consisting of cell toxicity sequence feature/motif, cell membrane binding motif, DNA binding motif, RNA binding motif, non-specific binding motif.

5. The method according to claim 1, wherein the first sequence features learned by the first neural network include at least one of 2D and 3D structural information, motif feature, physical and chemical property score of each sequence.

6. The method according to claim 1, wherein the sequences are selected from a group consisting of DNA, RNA, protein amino acids.

7. The method according to claim 1, wherein the sequences are protein amino acids.

8. The method according to claim 1, further comprising determining identities of the sequences by a sequencing process.

9. The method according to claim 1, wherein the experiment outcome includes information about interaction or non-interaction of the sequences of the molecules with a target of interest.

10. The method according to claim 1, wherein the experiment outcome relates to protein binding or gene editing efficiency.

11. The method according to claim 1, further comprising performing both a supervised machine learning and an unsupervised machine learning, wherein the supervised machine learning uses the first dataset and the unsupervised machine learning uses both the first dataset and a second dataset that is different from the first dataset.

* * * * *